United States Patent

Takezaki

[19]

[11] Patent Number: 5,968,436
[45] Date of Patent: Oct. 19, 1999

[54] METHOD OF FIXEDLY SUPPORTING BIOPSY SPECIMEN AND EMBEDDING CASSETTE

[76] Inventor: Teiji Takezaki, 9862-51, Ooaza Yuuki, Yuuki-shi, Ibaraki 307, Japan

[21] Appl. No.: 08/860,709

[22] PCT Filed: Feb. 1, 1996

[86] PCT No.: PCT/JP96/00196

§ 371 Date: Jul. 23, 1997

§ 102(e) Date: Jul. 23, 1997

[87] PCT Pub. No.: WO96/24041

PCT Pub. Date: Aug. 8, 1996

[30] Foreign Application Priority Data

Feb. 3, 1995 [JP] Japan .................................... 7-016903

[51] Int. Cl.⁶ .............................. B29C 45/15; B29C 70/70
[52] U.S. Cl. ......................... 264/250; 264/275; 206/455
[58] Field of Search ................................ 264/275, 271.1, 264/297.1, 297.8, 297.9, 250, 277; 53/25, 26; 206/455, 438, 470

[56] References Cited

U.S. PATENT DOCUMENTS

| | | |
|---|---|---|
| 236,383 | 1/1881 | Waldeck . |
| 1,952,528 | 3/1934 | Bedford . |
| 3,489,265 | 1/1970 | Puente ..................................... 206/455 |
| 3,596,317 | 8/1971 | Nicholson . |
| 3,733,768 | 5/1973 | Carls et al. .................................. 53/25 |
| 3,752,306 | 8/1973 | Thompson et al. .................... 206/47 A |
| 3,994,763 | 11/1976 | Sheath et al. ............................. 264/511 |
| 4,278,626 | 7/1981 | Atanasovski ............................ 264/40.1 |
| 4,724,110 | 2/1988 | Arnold .................................... 264/102 |
| 4,851,394 | 7/1989 | Kubodera .................................. 514/54 |
| 4,882,426 | 11/1989 | Motozato .................................. 536/114 |
| 5,044,500 | 9/1991 | Webber et al. .......................... 206/455 |
| 5,168,993 | 12/1992 | Yen ......................................... 206/455 |
| 5,263,579 | 11/1993 | Blackman ................................ 206/455 |
| 5,714,106 | 2/1998 | Yoda et al. .............................. 264/275 |
| 5,800,763 | 9/1998 | Hoppe et al. ............................ 264/255 |

FOREIGN PATENT DOCUMENTS

| | | |
|---|---|---|
| 59-183347 | 10/1984 | Japan . |
| 1140064 | 6/1989 | Japan . |
| 58528 | 2/1992 | Japan . |
| 523179A | 2/1993 | Japan . |

*Primary Examiner*—Angela Ortiz
*Attorney, Agent, or Firm*—Price, Heneveld, Cooper, DeWitt & Litton

[57] ABSTRACT

A method of fixedly supporting a biopsy specimen in an embedding cassette in a process for embedding a biopsy specimen sampled from the human body by a doctor for microscopic inspection, which method comprises putting the specimen in the cassette, pouring a fixedly supporting agent into the space surrounding the specimen to embed the specimen therein, and gelling the supporting agent in this state by immersing the same in a solution of a mannan gelating agent. The supporting agent to be used here is one obtained by dissolving purified mannan powder in a solvent prepared by adding an antiseptic to water. The embedding cassette to be used here comprises a lid and a container. The central portion of a flat frame is caused to protrude toward one side thereof to form a flat container. At least either the lid or the bottom of the container is formed of a transparent porous plate. A protruding edge is formed along the circumference of the opening of the container, the edge protruding toward the other side of the flat frame, and through holes communicating with both sides are formed in the flat frame in the periphery of the container.

10 Claims, 7 Drawing Sheets

20 thin section

31 liquid permeable sheet-like thin strip

FIG. 12

24 porous plate    22 lattice

METHOD OF FIXEDLY SUPPORTING BIOPSY SPECIMEN AND EMBEDDING CASSETTE

TECHNICAL FIELD

This invention relates to a method of fixedly supporting a biopsy specimen in an embedding cassette without permitting it to be degraded, of all the processes necessary for the diagnosis of a disease or determination of a treatment for the disease, the method comprises sampling a biopsy specimen from human body, embedding it and preparing a thin section slide therefrom to be inspected microscopically in a pathological laboratory. This invention also relates to an embedding cassette and a fixedly supporting agent necessary for execution of the method.

BACKGROUND ART

Conventionally, when engaged in a work necessary to achieve the object as described above, the clinician places a biopsy specimen into a flat cassette with a lid made of an opaque porous plate, closes the lid, puts the cassette into a capsule where an antiseptic agent has been placed that prevents the specimen from degrading, and sends the capsule to a pathological laboratory for inspection.

In the pathological laboratory, the tester takes out the embedding cassette from the capsule, opens the lid of the cassette, and compares the biopsy specimen therein with the description on a bill attached to the specimen, to confirm that the specimen properly coincides with the description. Then, he places again the specimen into the cassette, puts it in a vessel containing alcohol or xylene, and submits it to processes comprising dehydration, removal of fat, removal of alcohol, and immersing it in an embedding agent consisting of paraffin or a resin in succession.

Then, the tester opens the lid of the embedding container, picks up the biopsy specimen directly with a pair of forceps, and transfers it to another embedding plate prepared in advance. He places the bottom of the embedding cassette which is made of a porous plate above the biopsy specimen placed on the embedding plate, with some spacing therebetween, and pours an embedding agent consisting of molten paraffin or resin over the bottom, to embed the biopsy specimen together with a part of the embedding cassette with the embedding agent. In this state, the embedding agent is allowed to cool so that the biopsy specimen embedded together with the part of the embedding cassette in the embedding agent is hardened to form an embedded block.

Then, the pathologist cuts the biopsy specimen kept in the embedded block with a microtome together with the embedding agent, into thin sections, and examines them with a microscope.

The above described processes employing the conventional embedding cassette have following problems which remain to be improved.

Firstly, during embedding operation, the biopsy specimen is picked up directly with forceps before it is transferred to the embedding plate. This operation may distort the specimen locally by pressure, and inflict damages thereupon, which may interfere with proper treatment of the specimen for laboratory inspection.

Secondarily, if a plurality of specimens are placed in the embedding cassette in the order of sampling or according to sampled sites, they may be placed in a different arrangement from the original one by accident when they are transferred to a separate embedding plate. Further, while they are transferred to a separate embedding plate, they may be wrongly intermingled with biopsy specimens from a different embedding cassette, or some of them may be exchanged for wrong specimens from a different cassette. If such wrong operations happen, they would bring a grave effect on the results of microscopic inspection which takes place following the transference.

Thirdly, after being embedded, a part of the biopsy specimen necessary for inspection is cut by the pathologist with a microtome into thin sections which are then observed by microscopy. However, as the technician who is responsible for embedding the biopsy specimen and the pathologist are generally different persons, the technician finds it difficult to locate the part of the specimen which the pathologist would desire to inspect, and thus finds it difficult to place the biopsy specimen on the embedding plate so as to allow the pathologist to cut the desired part thereof with a microtome. In short, with the conventional method it is very difficult for the pathologist to cut rightly the part of the specimen necessary for inspection into thin sections.

Fourthly, each time the tester compares the biopsy specimen with the description on a bill attached thereto in the embedding cassette, he must open the lid of the cassette. This confirmation work requires a considerable time. In addition, when the lid is opened, the biopsy specimen may fall by accident from the cassette.

Fifthly, as the embedding cassette is partly composed of a porous plate, the biopsy specimen may be lost by flowing through a pore, when it is sufficiently small to pass through the pore.

As the sixth problem, the embedded block requires a certain thickness because it must withstand the pressure from the cutting edge of a microtome, when cut into thin sections. In a big hospital or laboratory a vast number of waste blocks are produced, and to make the most of the space necessary for their storage, they are laid one over the other. For them to be laid one over the other neatly, they should be made as thin as possible.

The first object of this invention is to dispense with the use of forceps or other mechanical means which, in conventional methods, are used to transfer a biopsy specimen to an embedding plate, and thereby to protect the specimen from distortion by pressure which may lead to local damages.

The second object is to prevent a plurality of biopsy specimens which are placed properly in an embedding cassette from being placed in a different arrangement from the original one when they are transferred to a separate embedding plate, or from being confounded with other wrong biopsy specimens.

The third object is to permit the pathologist to cut properly a part of biopsy specimen necessary for inspection into thin sections, and thereby to make a proper inspection on them.

The fourth object is to facilitate the work involved in conforming that the biopsy specimen placed in an embedding cassette corresponds rightly with the description on a bill attached to the specimen, and further to prevent the specimen from being lost by accident during this confirmation work.

The fifth object is to prevent the biopsy specimen from flowing through a pore of the porous plate of an embedding cassette.

The sixth object is to reduce the thickness of an embedded block while maintaining its mechanical strength.

DISCLOSURE OF INVENTION

This invention relates to a procedure comprising: placing a biopsy specimen in the interior of a flat embedding cassette which has at least a lid or a bottom made of a transparent porous plate, filling a fixedly supporting agent consisting of glucomannan and an antiseptic around the biopsy specimen thereby fixing the specimen so as not to undergo degradation and at the same time to stabilize the specimen in the embedding cassette, and immersing the assembly into a gelating agent such as alcohols or acetone supplemented with a putrefaction preventing agent contained in a capsule, thereby to harden the biopsy specimen contained in the embedding cassette.

The biopsy specimen thus fixed and supported in the embedding cassette is immersed in alcohol while being kept in the embedding cassette, to be removed of water and fat, and then immersed in xylol to be removed of alcohol (to be cleared). The specimen fixed and supported is taken out as a gel block embedded in the fixedly supporting agent from the embedding cassette, and placed on an embedding plate.

Then, above the gel block put on the embedding plate is placed the container of the embedding cassette which has been left vacant after removal of the biopsy specimen, opposite to the block with a slight gap in between. Then, an embedding agent consisting of molten paraffin or resin is poured from above onto the container until it fills the whole capacity of the container, and is allowed to cool and harden. Through this operation, in the embedding agent are embedded the biopsy specimen fixed by the fixedly supporting agent, and the container of the embedding cassette.

Further, this invention relates to a fixedly supporting agent for a biopsy specimen which is obtained after purified mannan powder has been dissolved in a solvent which comprises water supplemented with an antiseptic.

Furthermore, this invention relates to an embedding cassette for a biopsy specimen comprising a lid and a container, in which a flat frame protrudes its central portion towards one side of the frame to form a flat container, at least the lid or the bottom is made of a transparent porous plate, the flat frame around the mouth of the container has a vertical edge on the other side, and the flat frame around the container has a passage communicating the two sides.

BEST MODE FOR CARRYING OUT THE INVENTION

This invention will be described below with reference to attached drawings.

Figure 1:
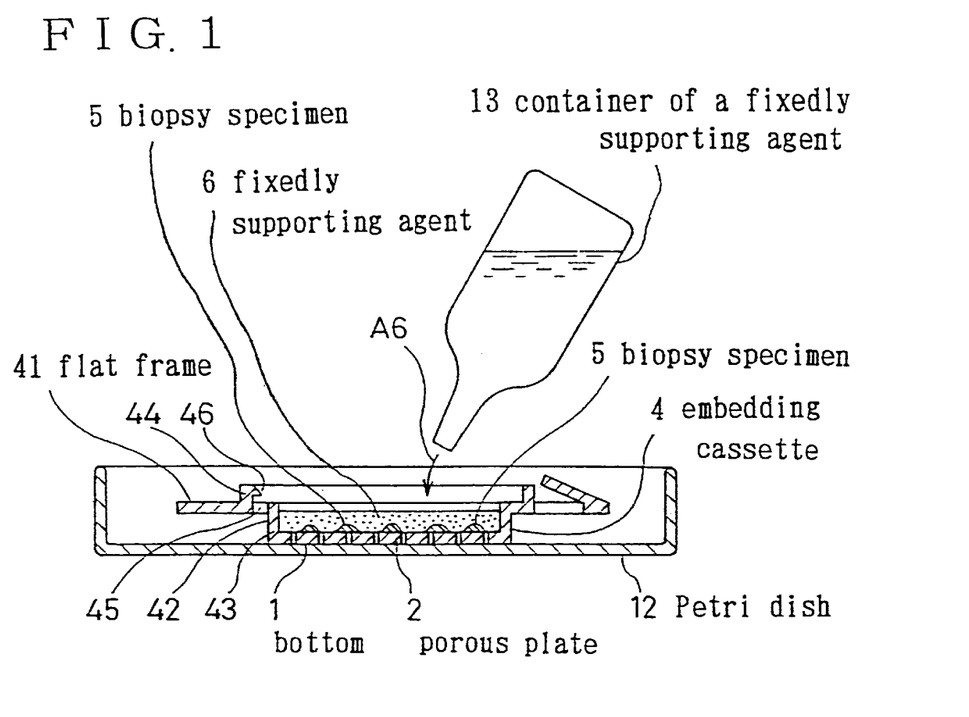
FIG. 1 gives a longitudinal cross-section of the embedding cassette illustrating how the fixedly supporting agent is poured in one example exhibiting the fixation procedure of a biopsy specimen according to this invention.

Firstly, as shown in FIG. 1, the container 42 of an embedding cassette 4 is put on a petri dish 12, and then biopsy specimens 5 are placed in the interior of the container 42. A fixedly supporting agent 6 consisting of purified, water-soluble fibrous mannan (natural polysaccharide glucomannan) and an antiseptic such as formalin is poured from a vessel 13 containing the fixedly supporting agent 6 as shown by the arrow A6 until it fills the space over and around the biopsy specimens 5. This supporting agent allows the biopsy specimens 5 to be fixed without degrading, and to be stabilized in the interior of the container 42 of the embedding cassette 4.

Figure 2:
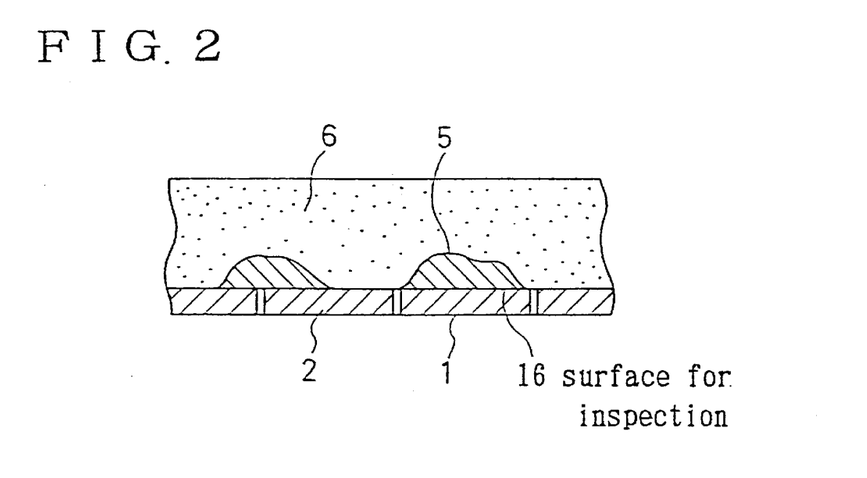
FIG. 2 gives an enlarged cross-section of a part of the cassette shown in FIG. 1.

Just prior to this operation, as shown in FIG. 2, the biopsy specimens 5 have their surfaces 16 which the clinician wants to be examined placed in contact with the bottom 1 of the container 42.

The embedding cassette 4, as seen from FIGS. 3 and 4, and FIGS. 10–12, consists of the flat container 42 which is formed after the central portion of an oblong flat frame 41 is allowed to protrude downward to form a lower rim 43, and of a lid 3, and at least the lid 3 or the bottom 1 of the container 42 is made of a transparent porous plate 2.

Around the mouth of the container 42 is attached a flat frame 41 on the top surface of which stands a vertical edge 44, and the flat frame 41 surrounding the container 42 has a passage 45 which connects the upper and lower surfaces.

Figure 10:
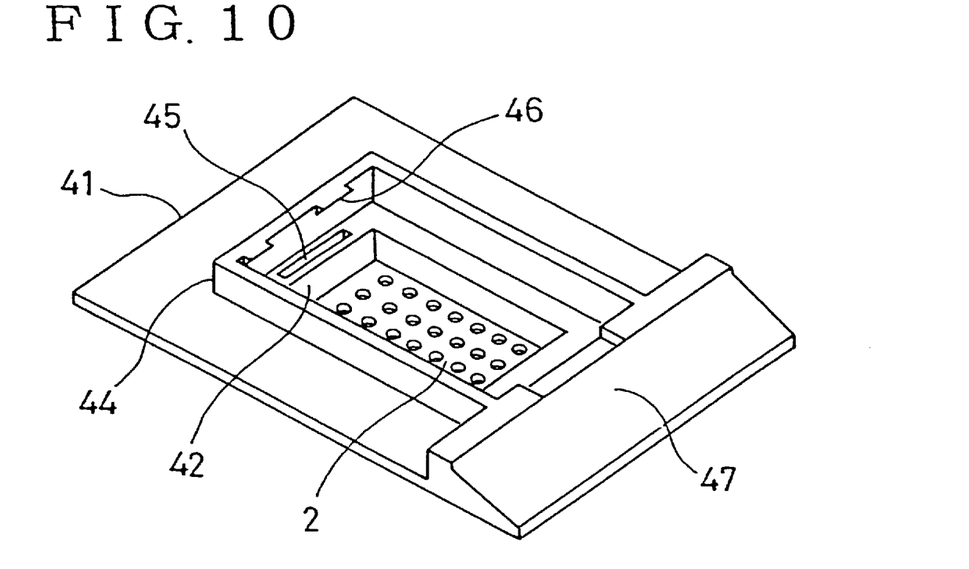
FIG. 10 gives a perspective view of one example of the embedding cassette of this invention.

On one edge of the container 42 are formed anterior stoppers 46, while on the opposite edge are formed posterior stoppers 47, and thanks to those stoppers, the lid 3 can be removably fitted to those stoppers.

The fixedly supporting agent is obtained as follows: konnyaku (=arum roots) whose black skin has been removed thoroughly are ground to produce crude powder which is then purified by blowing to produce purified mannan, 8.4 g of purified mannan is dissolved in 1000 ml of 10% neutral buffered formalin which contains 100 ml of undiluted formalin, 4.0 g of sodium dihydrogen phosphate (Na $H_2PO_4 \cdot H_2O$), 6.5 g of anhydrous disodium hydrogen phosphate ($Na_2H\ PO_4$), and 900 ml of distilled water.

The water-soluble edible fibers which constitute an ingredient of thus obtained fixedly supporting agent readily allow passage of fluid owing to their structure and inherent property, and do not stain even when exposed to various kinds of staining agents. Accordingly, they help the biopsy specimens to be distinguished clearly after the specimens are stained, and do not interfere with the proper observation of those stained specimens.

Fixation due to the fixedly supporting agent consists of fixing a raw tissue by making use of congealing property of proteins thereby to prevent the tissue from degrading over time, and of preserving the morphology of components of the biopsy specimen as close as possible to what they are in a living body. Supporting refers to securely stabilize the biopsy specimen in a proper place on the bottom of the embedding cassette by bonding it thereupon, so that the specimen will not move in the interior of the embedding cassette.

Figure 3:
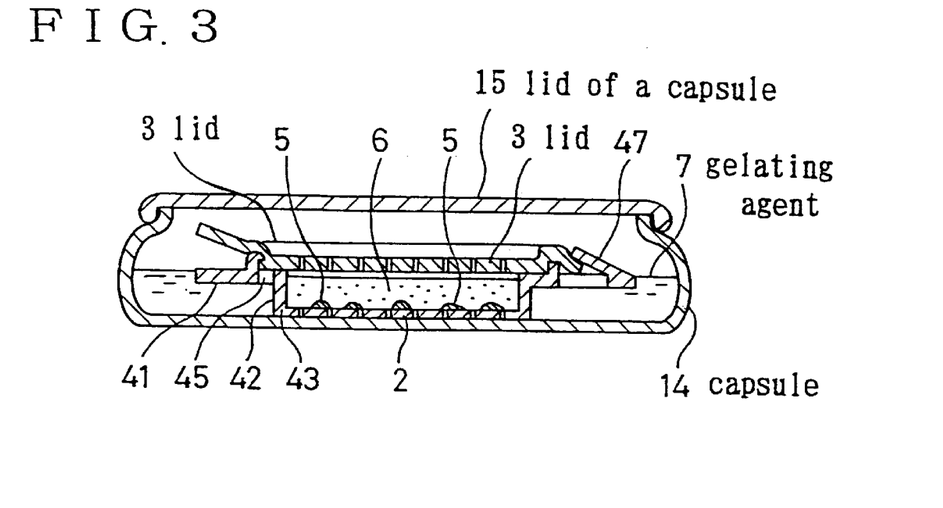
FIG. 3 gives a longitudinal cross-section illustrating how gelation proceeds according to the above procedure.

The lid 3 is fitted to the container 42 kept at the state as illustrated in FIG. 1, and the assembly, as shown in FIG. 3, is immersed in a gelating agent 7 consisting of 50% methanol and formalin contained in a capsule 14 with a lid 15, to gelate the fixedly supporting agent 6. Through this operation, the biopsy specimens 5 are firmly supported in the container 42 of the embedding cassette 4 and can be sent, for example by mail, from a clinic to a pathological laboratory.

The gelating agent 7 of glucomannan includes, for example, alcohol formalin, alcohol, acetone, polyethylene glycol, glycerin, etc.

Figure 4:
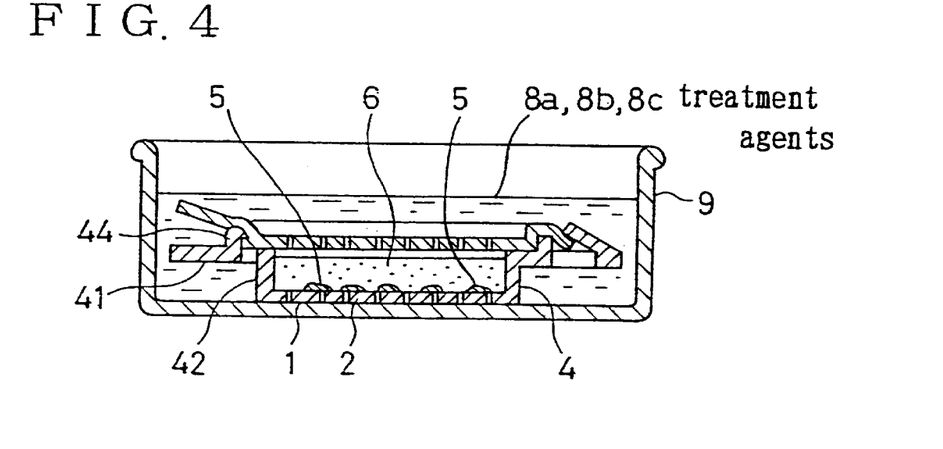
FIG. 4 gives a longitudinal cross-section illustrating how the specimen is removed of water and fat, and cleared of alcohol to be ready for penetration by an embedding agent according to the above procedure.

In the pathological laboratory, from the capsule 14 is taken out the embedding cassette 4 where the biopsy specimens 5 have been firmly fixed, which is then immersed, as shown in FIG. 4, in a highly dehydrating agent 8a such as alcohol which has been stored in a treatment vessel 9. Later, it is immersed in a fat removing agent 8b and an alcohol clearing agent 8c (not illustrated here) in succession, to undergo dehydration, fat removal and alcohol clearing. Then, the fixedly supporting agent and biopsy specimens in a gelated state are infiltrated by an embedding agent consisting of paraffin or a resin.

Figure 5:
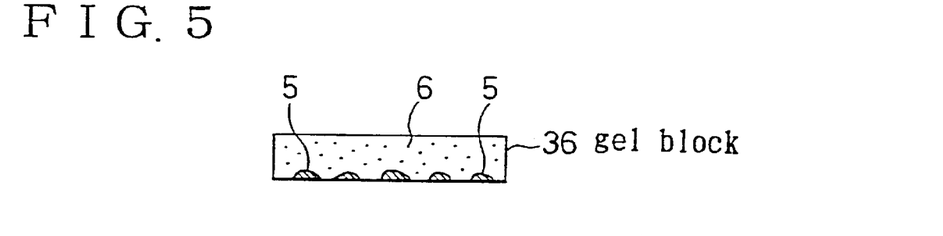
FIG. 5 gives a longitudinal cross-section illustrating how the biopsy specimen is embedded in a fixedly supporting agent according to the above procedure.

Then, the embedding cassette 4 is removed from the treatment vessel 9, and the biopsy specimens 5 are removed from the embedding cassette 4 while they are being embedded in the fixedly supporting agent 6 as a gel block 36 as shown in FIG. 5. The block is then put on an embedding plate 10 with its surface for inspection facing downward as shown in FIG. 6.

Figure 6:
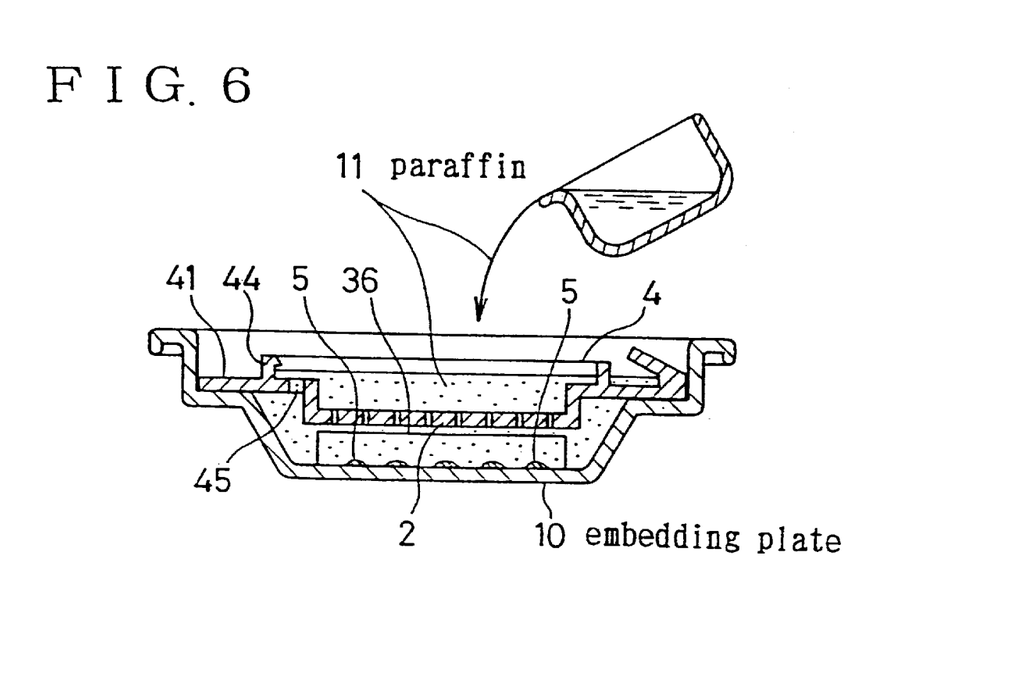
FIG. 6 gives a longitudinal cross-section illustrating how the biopsy specimen prepared according to the above procedure is embedded.

Further, as shown in FIG. 6, above the gel block 36 is placed the container 42 which remains empty after the biopsy specimens have been removed, with a slight spacing there between, and with its bottom facing the block 36. Molten paraffin 11 is poured from above the container 42 until it totally covers the container 42. Then the paraffin 11 is allowed to cool and harden. Thus, the biopsy specimens 5 kept in the fixedly supporting agent are embedded in the hardened paraffin 11 together with the container 42 of the embedding cassette 4.

Paraffin 11 enters through pores of a porous plate 2 and the passage 45 into the space bounded with the outer surfaces of the gel block 36 and the under surface of the flat frame 41 until it completely fills that space. A synthetic resin and paraffin can be readily removed from each other owing to their inherent properties even when they are bonded closely together. However, because, with above arrangement, paraffin 11 hardens after having passed through pores of the porous plate of the container 42 and the passage 45, paraffin in the upper and lower spaces harden together with the container 42 as a partition. Therefore, paraffin and the container are too firmly fixed to each other to be removed.

As the under surface of the flat frame 41 closely fits to the inner surface of the embedding plate 10, and the flat frame 41 has a vertical edge 44, paraffin is prevented from flowing over the upper surface of the flat frame 41. Accordingly, paraffin 11 does not adhere to the upper surface of the flat frame 41 or its edge, and, when the embedded block is mounted to the platform 19 of a microtome, paraffin 11 will not touch the platform, and hence not interfere with the work involved in block mounting.

Figure 7:
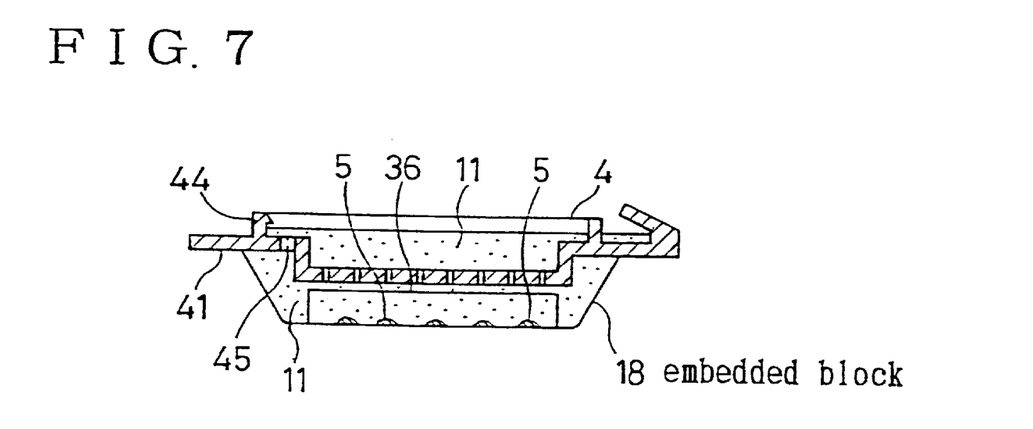
FIG. 7 gives a longitudinal cross-section illustrating the state of the biopsy specimen after it has completed the embedding process as depicted in FIG. 6.

After paraffin 11 has hardened, the embedding plate 10 is removed to produce an embedded block 18 as shown in FIG. 7 which comprises the biopsy specimens 5 embedded in paraffin 11 together with the container 42 of the embedding cassette 4.

Figure 8:
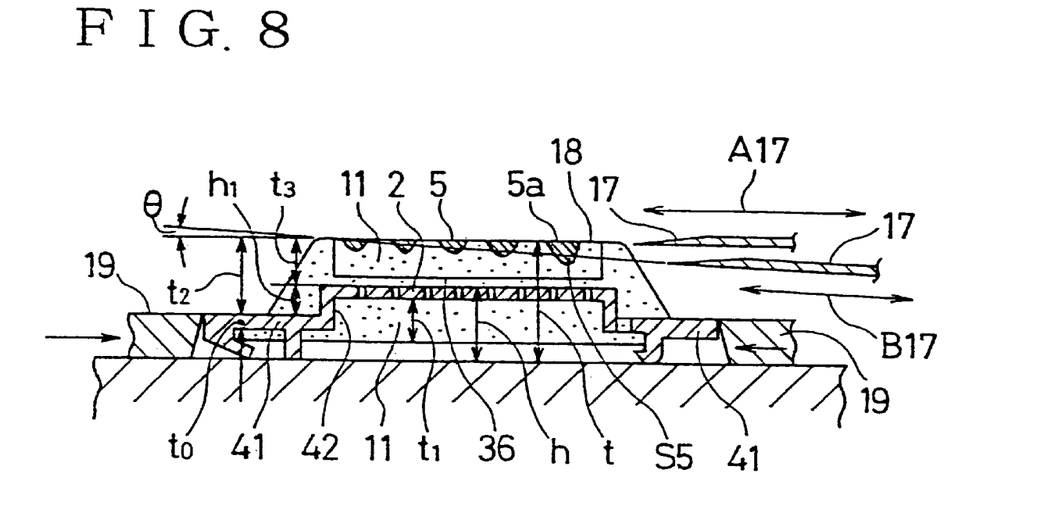
FIG. 8 gives a longitudinal cross-section illustrating how the biopsy specimen is cut into thin sections.
Figure 9:
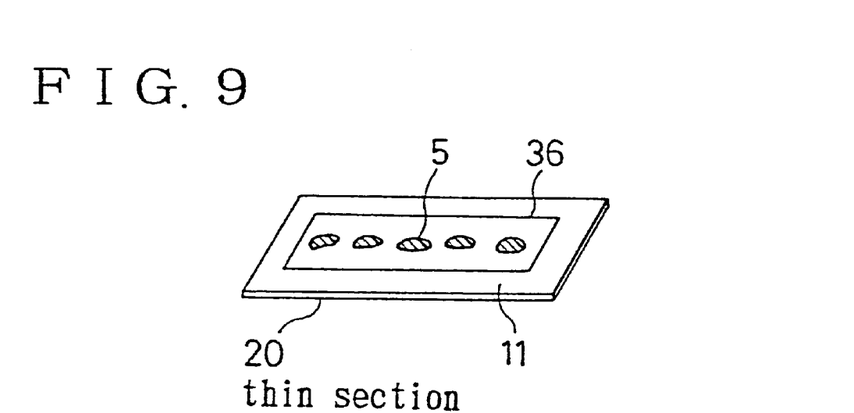
FIG. 9 gives an array of thin sections obtained from the embedded block in FIG. 8.

Then, as shown in FIG. 8, the embedded block 18 is placed properly on the platform 19 so that its surface to be cut faces upward and is fixed. The cutting edge 17 of a microtome is moved back and forth in the direction as shown by the arrow A17 to slice the block and thereby to produce thin sections 20 of the biopsy specimens as shown in FIG. 9.

As shown in FIG. 8, it is necessary to adjust the height h of the embedding cassette 4 made of a resin so that the embedded block 18 fixed with supporting members 19 and 19 is practically free from any distortions, or can maintain its rigid form even while it is sliced with the cutting edge 17. Assuming that the embedding cassette 4 has a wall thickness $t_0$ of 1.5 mm, the height h should be 5 mm or more.

Further, in this case, for the container 42 and paraffin 11 to be sufficiently strong to be bonded firmly together, the paraffin 11 within the container 42 should have a thickness $t_1$ of 3.5 mm or more.

Furthermore, when the embedded block 18 is sliced with the cutting edge 17 as described above, and a specific cut surface $S_5$ of a biopsy specimen 5a among the biopsy specimens 5 is desired, it is necessary to give a slightly slanting angle θ to the cutting edge 17 with respect to the direction as shown by the arrow A17, and to allow the edge to move back and forth in that direction shown by the arrow B17. During this operation, when the edge 17 approaches the top surface of the platform 19, its smooth movement may be interfered on account of the existence of the platform. For the top surface of the platform not to stand in the way of the edge 17, it is necessary to give paraffin 11 a height of 6 mm or more when measured from the top surface of the platform 19. As shown in the figure, the flat frame 41 bonded to the embedded block 18 has the same height with the top surface of the platform 19, and hence, as is discussed above, it is necessary to allow paraffin 11 to have a thickness $t_2$ of 6 mm or more when measured from the flat frame.

The total thickness t of the embedded block can be calculated as follows:

When the height $h_1$ of the protruding container 42 is subtracted from the thickness $t_2$ of paraffin 11 growing above the frame 41 around the container 42, the height of paraffin 11 growing above the bottom of the container is obtained which is termed as $t_3$. Then, the total thickness t of the embedded block is the sum of the height h of the embedding cassette 4 and the thickness $t_3$ of paraffin 11, and can be expressed by the following equation:

$$t=h+t_3, \text{ or alternatively, } t=h+(t_2-h_1) \tag{1}$$

When the symbols in the equation (1) are substituted by appropriate physical dimensions which are necessary to give a sufficient strength to the embedding block, that is, h by 5 mm, $t_2$ by 6 mm and $h_1$ by 2.5 mm, then the total thickness t of the embedded block will be t=5 mm+(6 mm−2.5 mm)=8.5 mm.

Figure 15:
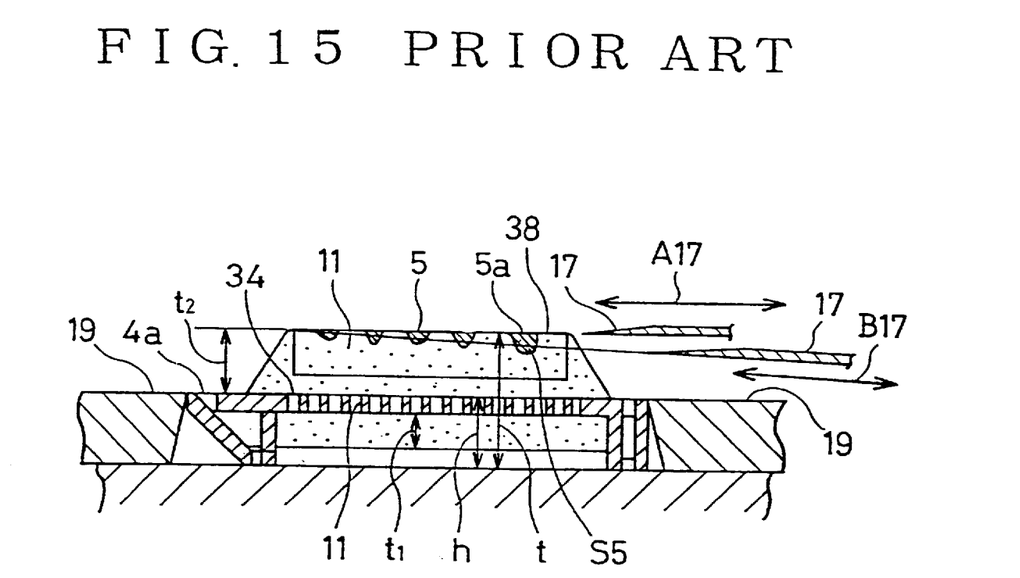
FIG. 15 gives a longitudinal cross-section of the embedded block derived from the embedding cassette of FIG. 13, illustrating the operation corresponding with that shown in FIG. 8.

Let's see what thickness an embedded block 38 will have when it is prepared by the same method with, however, a conventional embedding cassette 34 as shown in FIG. 15. The embedded block 38 in this case does not have a height corresponding with hi shown in FIG. 8. As $h_1=0$, the thickness t of the embedded block 38 in FIG. 15 is t=5 mm+6 mm=11 mm.

When the thickness t of the embedded block 18 prepared according to this invention is compared with the corresponding thickness of the embedded block prepared according to the conventional method, the difference is 11 nm−8.5 mm=2.5 mm. In short, according to the foregoing example, the embedded block 18 of this invention can be thinner by 2.5 mm than that prepared by the conventional method, even though being the same in mechanical strength with the latter.

This allows a huge number of embedded blocks (for example, several ten thousands blocks) prepared according to this invention to be stored in a far smaller space than is possible with the blocks prepared by the conventional method, when they are laid one over the other for storage.

Figure 13:
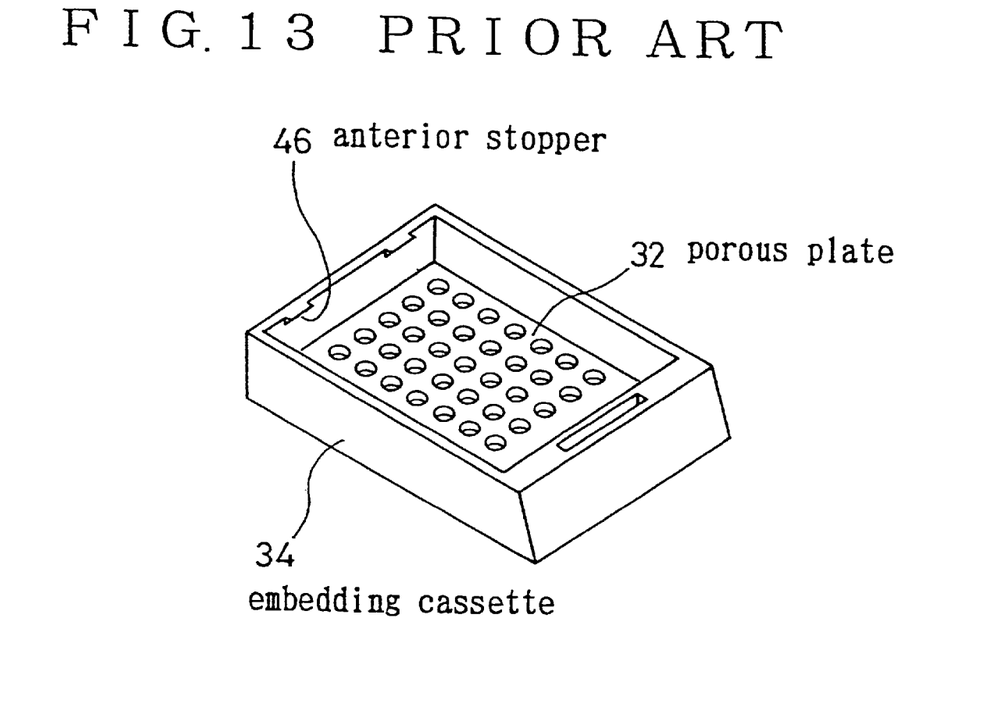
FIG. 13 gives a perspective view of a conventional embedding cassette.
Figure 14:
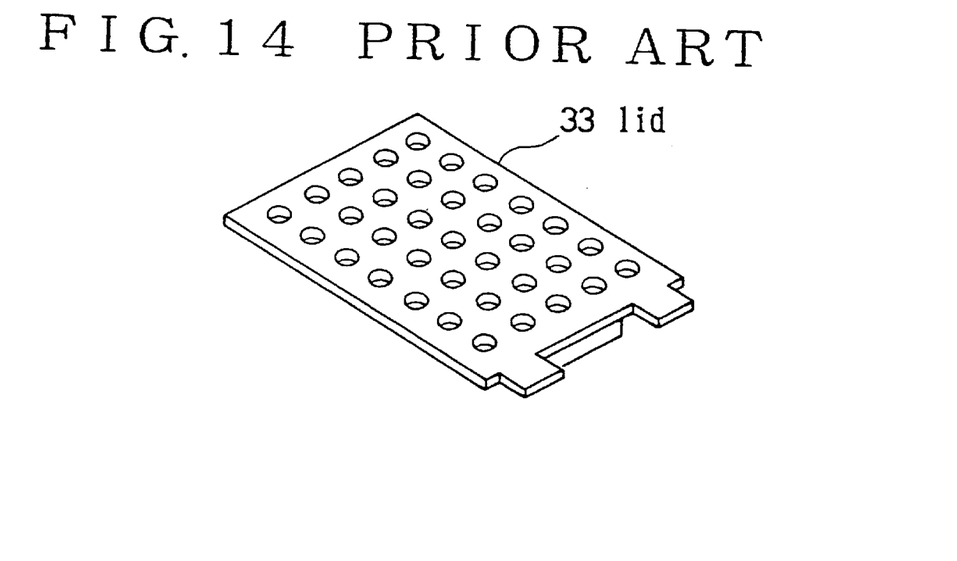
FIG. 14 gives a perspective view of a lid which is used for the embedding cassette in FIG. 13.

It should be added here that a porous plate 32 in FIG. 13 and a lid 33 in FIG. 14 corresponds respectively with the porous plate 2 and lid 3 of this invention.

A number of examples according to this invention have been described with reference to FIGS. 1–8 and FIG. 10, but this invention should not be limited to those examples. It should be understood that it is possible to add amendments and modifications to this invention without trespassing the scope of this invention.

Figure 11:
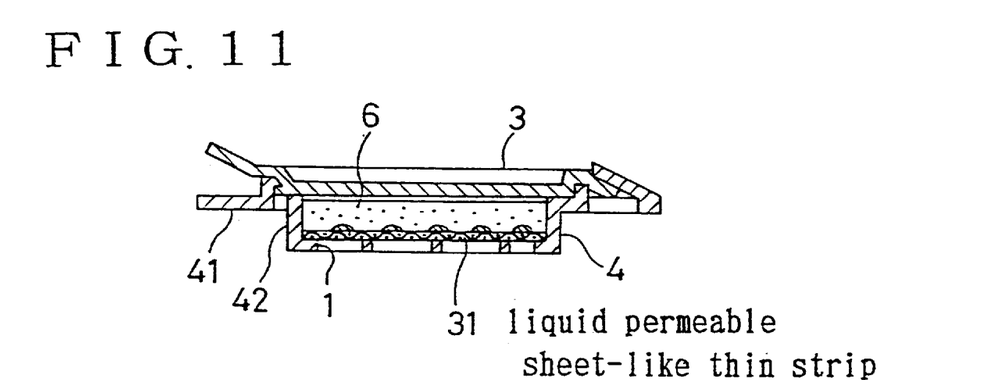
FIG. 11 gives a longitudinal cross-section of a second embedding cassette of this invention corresponding in profile with that shown in FIG. 1.

For example, the bottom 1 of the container 42 of the embedding cassette 4 can be prepared, instead of a transparent material as in the foregoing examples, by placing a lattice 22 with windows 21 at the central part thereof, and fitting snugly a thin sheet 31 made of a porous material and permeable to liquids to the lattice.

In this case, the liquid-permeable sheet-like thin strip 31 may include liquid permeable cloth, or washi(=Japanese paper prepared from plant thin stem fibers prepared by a Japanese traditional method) (not illustrated here).

It should be noted here that the numerals and symbols in FIG. 11, and FIG. 12 which will be described later are the same in meaning and function with those appearing in the foregoing examples.

Figure 12:
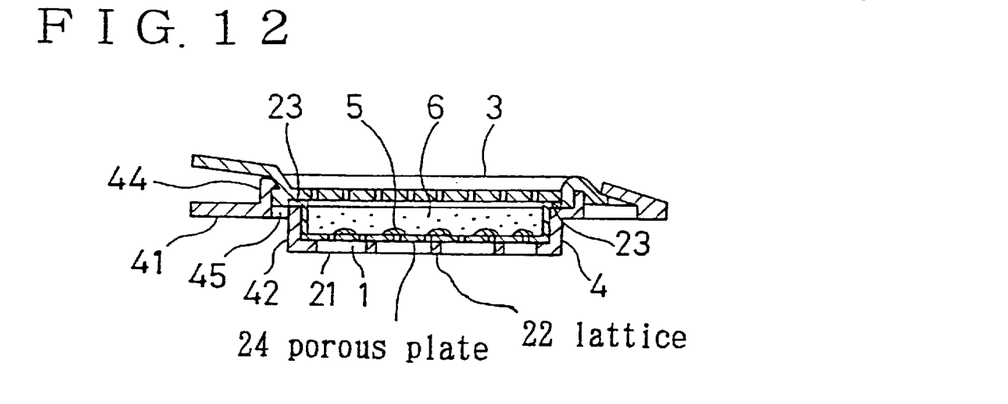
FIG. 12 gives a longitudinal cross-section of a third embedding cassette put in the same state as that in FIG. 10.

The liquid-permeable sheet-like thin strip 31 is snugly fit to windows 21 as shown in FIG. 11, but they can be replaced with a porous plate 24 as shown in FIG. 12 which is snugly fit to windows 21 by hooking its flange 23 on the periphery of the windows 21.

The fixedly supporting agent 6 can be obtained as follows besides those in the foregoing examples: Konnyaku (=arum roots) whose black skin has been removed thoroughly are ground to produce crude powder which is then purified by blowing to produce purified mannan, and 8.4 g of purified mannan is dissolved in 1000 ml of 20% formalin saline which contains 200 ml of undiluted formalin and 800 ml of saline.

The antiseptic to be used in combination to produce the fixedly supporting agent 6 may include, besides those in the foregoing examples, formaldehyde, paraformaldehyde, glutar aldehyde, glacial acetic acid, thymol, creosote, cresol, etc.

Furthermore, although the foregoing examples concern with the method wherein molten paraffin 11 is used as an embedding agent and allowed to cool and harden specimens, the embedding should not be limited to that method. Two alternative methods can be cited as a further example.

One method is called paraplast-piccolyte duplicate embedding. The method consists of grinding white piccolyte or a carbohydrate resin with a high melting point (about 115° C.) which has been synthesized from terpene β-pinene, in a mortar, dissolving the resulting powder in molten paraplast heated at 60° C. to give a 10% solution, cooling the solution to harden, and storing it. As another run, a biopsy specimen supported by glucomannan (fixedly supporting agent) is dehydrated and infiltrated by paraffin, and embedded, during the final stage of embedding, with molten paraplast-piccolyte: the hardened paraplast blended with 10% piccolyte is heated at a temperature maintained below 60° C., and the biopsy specimen is placed in that solution for embedding.

The other method is called historesin-plus (Leica) embedding and consists of following steps ①–⑧:
① A biopsy specimen is fixed with gelatinized glucomannan, and dehydrated with any one of alcohol, acetone or glycol methacrylate(GMA).
② A 100 ml of basic resin (HEMA: dihydroxyethyl methacrylate and hydroxy ether as a plasticizer) and 0.6 g of activator benzoylperoxide (reaction starter: peroxydol CH50) are combined and the mixture is cooled to 4° C. to produce a historesin-plus solution.
③ The biopsy specimen supported with the fixedly supporting agent is immersed in the historesin-plus solution A cooled at 4° C.
④ Then, 1 ml of hardener is added to 30 ml of the historesin-plus solution A (at 4° C.) and mixed at 4° C. to produce a historesin-plus solution B.
⑤ The biopsy specimen supported with the fixedly supporting agent and kept in the historesin-plus solution A (at 4° C.) is immersed in the historesin-plus solution B, and is stirred at 4° C. for five minutes.
⑥ The historesin-plus solution B maintained at 4° C. is poured in to a mold tray for embedding being cooled in advance, and the biopsy specimen supported with the fixedly supporting agent is so placed as to allow its surface for inspection to face downward.
⑦ Immediately thereafter, PE foil (or film) is laid over the resin block embedding the biopsy specimen to wrap it up completely. During this operation, historesin-plus will not harden because oxygen will interfere with the polymerization of the resin in question (hardening of this resin through polymerization will require three hours or longer at 4° C.)
⑧ Then, the resin hardened as a result of polymerization and containing the biopsy specimen is fixed on a block holder (or a platform).

This invention as described above exhibits the following advantages:

First, this invention allows the tester, when he transfers a biopsy specimen from an embedding cassette to a separate embedding plate, to hold the specimen through the fixedly supporting medium surrounding it instead of picking it up directly with forceps, which will protect the specimen from undue damages and thus will ensure proper treatment of the specimen in subsequent processes leading to laboratory tests.

Second, this invention protects the tester, when he transfers biopsy specimens from an embedding cassette to an embedding plate, from the risk of placing the specimens in a wrong plate, or of confounding them with specimens from other cassettes. Thus, the transference of biopsy specimens from an embedding cassette to an embedding plate will proceed properly, having no grave effect on the laboratory test results by microscopy in subsequent processing of those specimens.

Third, this invention allows the tester to properly slice the part of an embedded biopsy specimen necessary for inspection, which will ensure proper testing of that specimen.

Fourth, this invention allows the tester to easily confirm that a biopsy specimen placed in an embedding cassette corresponds rightly with the description on a bill attached thereto, without opening the lid of the cassette, because at least the lid or the bottom of the embedding cassette is made of a transparent porous plate. This arrangement further protects the tester from the risk of losing the biopsy specimen by accident.

Fifth, this invention eliminates the risk that a biopsy specimen may be lost by flowing through a pore of the porous plate of an embedding cassette.

Sixth, this invention allows an embedded block to have a smaller thickness than that prepared by a conventional method. Therefore, when it is necessary to store a huge number (for example, of the order of several ten thousands) of such blocks, the space necessary for storage of them can be made far smaller than is possible with the blocks prepared by the previous method.

Industrial Applicability

As is evident from above description, this invention is adapted for properly placing biopsy specimens in an embedding cassette. Further, this ensures smooth operation of a series of work involved in embedding because it protects the biopsy specimens from the risk of being lost, of being damaged and of being confounded with other specimens. Thus, this invention is adapted for the proper testing of a biopsy specimen which has been prepared through following processes: the pathologist samples the biopsy specimen, the tester or a person other than the pathologist embeds it, and the pathologist slices the embedded biopsy specimen into thin sections, to examine them.

This invention further allows a place with a constant space to store a far larger number of embedding cassettes than is possible with conventional embedding cassettes, which will relieve the personnel in charge of considerable cost involved in their storage.

I claim:

1. A method for fixedly supporting a biopsy specimen comprising:

placing the biopsy specimen in a flat embedding cassette for embedding the biopsy specimen therein together with the flat embedding cassette so as to form an embedded block, wherein said flat embedding cassette includes a container and a lid, and at least one of the lid and container is made of a transparent porous plate, injecting a fixedly supporting agent comprised of mannan and an antiseptic into a space around the biopsy specimen for fixing a raw tissue of the biopsy specimen to prevent it from degrading and also for securely supporting the biopsy specimen in a proper place in the embedding cassette by preventing it from moving around therein, embedding the biopsy specimen in the fixedly supporting agent, and immersing the fixedly supporting agent incorporating the biopsy specimen in a solution containing a gelating agent of mannan, to gelate the fixedly supporting agent.

2. The method according to claim 1, wherein said fixedly supporting agent of biopsy specimens is produced by dissolving purified mannan powder in a solvent prepared by adding an antiseptic to water.

3. The method according to claim 2, wherein the antiseptic to be added to water contains at least formaldehyde.

4. An embedding cassette for biopsy specimens for embedding a biopsy specimen therein together with the flat embedding cassette so as to form an embedded block, said embedding cassette having a lid and a container comprising:

a flat frame which protrudes its center towards one side of the frame to form a flat container;

at least one of the lid and bottom of the container is made of a transparent porous plate;

the flat frame around a mouth of the container has a vertical edge on the other side; and the flat frame around the container has a passage communicating the two sides.

5. The embedding cassette for biopsy specimens according to claim 4, wherein the bottom of the container which is made of a transparent porous plate, has its central portion formed into a lattice with windows, and has a liquid-permeable thin strip fitted to those windows.

6. The embedding cassette for biopsy specimens according to claim 4, wherein bottom of the container is formed after a liquid-permeable thin strip prepared from a transparent porous sheet made of a synthetic resin has been fitted to windows on a lattice formed at the central portion of the bottom.

7. The embedding cassette for biopsy specimens according to claim 4, wherein the bottom of the container is formed after a liquid-permeable thin strip prepared from transparent textile has been fitted to windows on a lattice formed at the central portion of the bottom.

8. The embedding cassette for biopsy specimens according to claim 6, wherein the liquid-permeable porous thin strip to be fitted to the windows of the lattice is a porous plate with a flange around its periphery.

9. A method for fixedly supporting a biopsy specimen comprising:

placing a biopsy specimen in a flat embedding cassette for embedding the biopsy specimen therein together with the flat embedding cassette to form an embedded block, wherein said flat embedding cassette has a container and a lid;

injecting a fixedly supporting agent comprised of mannan and an antiseptic into a space around the biopsy specimen for fixing a raw tissue of the biopsy specimen to prevent it from degrading and also for securely supporting the biopsy specimen in a proper place in the embedding cassette by preventing it from moving around therein;

embedding the biopsy specimen in the fixedly supporting agent;

immersing the fixedly supporting agent incorporating the biopsy specimen in a solution containing a gelating agent of mannan to gelate the fixedly supporting agent;

removing the gelated fixedly supporting agent incorporating the biopsy specimen from the embedding cassette as a gel block; and immersing the gel block in an embedding agent.

10. The method as defined in claim 1, wherein said fixedly supporting agent is transparent.

* * * * *